United States Patent [19]

Lipner

[11] Patent Number: 4,576,599
[45] Date of Patent: Mar. 18, 1986

[54] SANITARY PADS FOR MEN

[75] Inventor: Harry Lipner, Tallahassee, Fla.

[73] Assignee: Florida State University, Tallahassee, Fla.

[21] Appl. No.: 609,651

[22] Filed: May 14, 1984

[51] Int. Cl.$^4$ ............................................. A61F 13/16
[52] U.S. Cl. ................................ 604/390; 604/385 R; 604/389; 604/352
[58] Field of Search ............... 604/346, 347, 349, 352, 604/358, 385 R, 389, 390; 128/168

[56] References Cited

U.S. PATENT DOCUMENTS

| | | | |
|---|---|---|---|
| 2,891,546 | 6/1959 | Galloway | 604/352 |
| 3,871,378 | 3/1975 | Duncan et al. | 604/372 |
| 3,939,836 | 2/1976 | Tunc | 604/364 |
| 4,064,880 | 12/1977 | Logan | 604/358 |
| 4,182,334 | 1/1980 | Johnson | 604/385 |
| 4,244,367 | 1/1981 | Rollenhagen | 604/396 |

Primary Examiner—William R. Dixon, Jr.
Assistant Examiner—Ann M. Knab
Attorney, Agent, or Firm—Dennis P. Clarke

[57] ABSTRACT

Sanitary pads for men are disposable in a storage mode in which they are flat and non-overlapping for easy carrying in pockets. The sanitary pads may be folded in order to form generally semi-cylindrical portions which envelop the wearer's penis and prevent embarrassment to incontinent men. In the storage or carrying mode, the pad may alternately be T-shaped or constructed in a generally rectangular shape. Adhesive means, such as double sided tape, or fabric loop and hook fasteners may be used to secure the pads in proper position. The pads are a layered structure including an inner relatively thick layer of absorbent material, a water barrier layer made of plastic, and an outer relatively thin absorbent layer.

12 Claims, 8 Drawing Figures

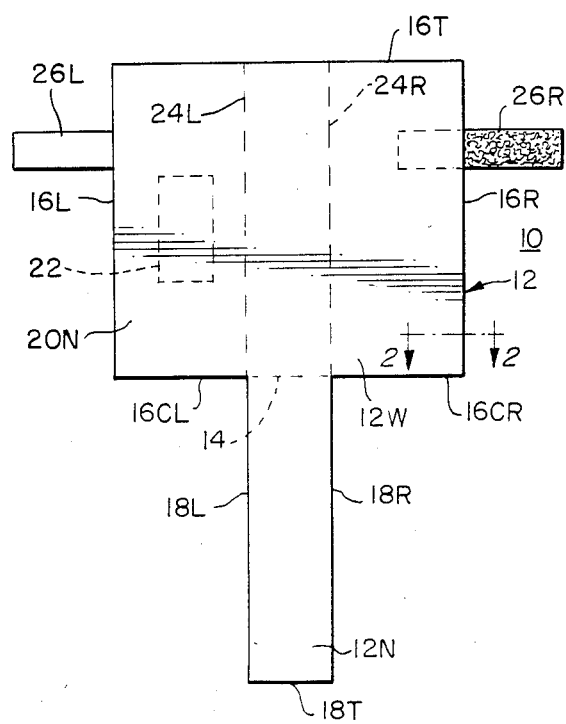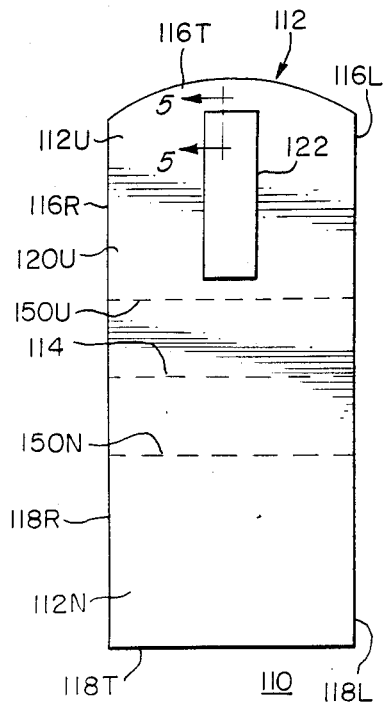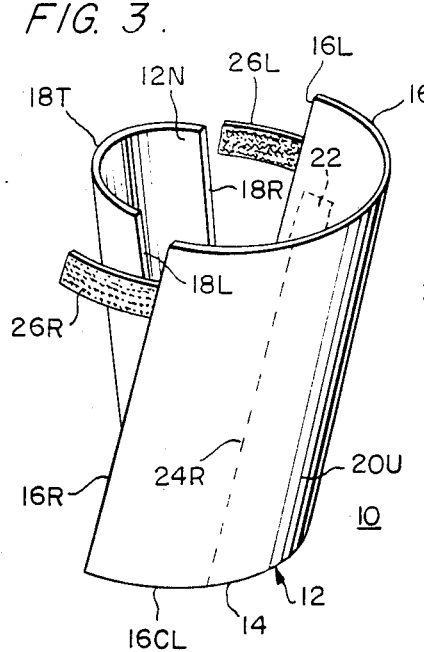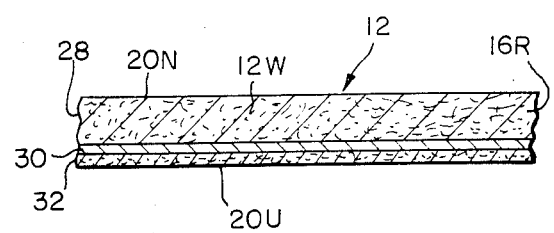

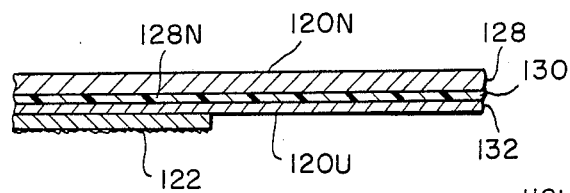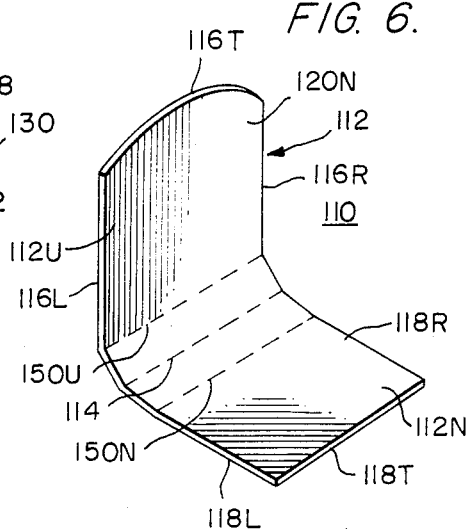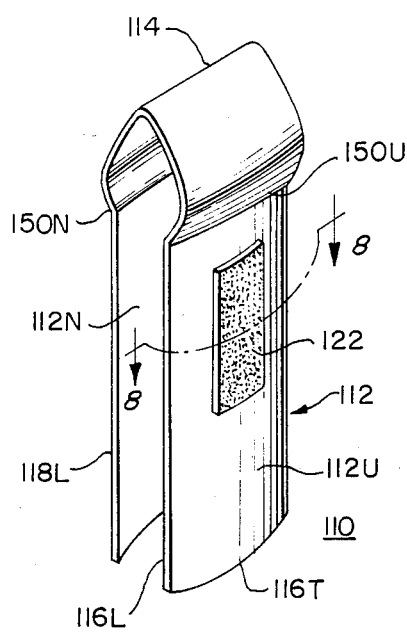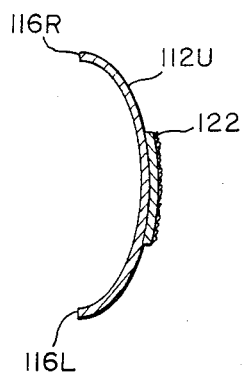

SANITARY PADS FOR MEN

BACKGROUND OF THE INVENTION

This invention relates to sanitary pads for men.

The use of sanitary pads by women is almost universal in modern society. Such pads are, of course, used by women during menstruation.

The use of sanitary pads by men is relatively uncommon. However, numerous male problems varying from involuntary ejaculation, partial incontinence due to benign prostatic hyperplasia and post urination drip can be helped by sanitary pad protection. The problem of partial incontinence is relatively common among older men.

The use of a sanitary pad for men is disclosed in U.S. Pat. No. 4,064,880, issued to Logan on December 27, 1977. Specifically, this patent discloses various embodiments of tubular made sanitary napkins. Adhesive may be used to hold the sanitary napkins together. The sanitary napkins may be stored with parts of the tube folded under and in between other parts of the generally cylindrical tube shape.

The following additional U.S. Patents disclose other sanitary napkins or fabric constructions:

| U.S. Pat. No. | Inventor | Issue Date |
| --- | --- | --- |
| 3,871,378 | Duncan et al | Mar. 18, 1975 |
| 3,939,836 | Tunc | Feb. 24, 1976 |
| 4,182,334 | Johnson | Jan. 8, 1980 |
| 4,244,367 | Rollenhagen | Jan. 13, 1981 |

The Duncan et al patent shows an absorbent bandage or sanitary napkin which is shaped to conform to a women's anatomy and may be used for incontinence. The structure uses an absorbent core material and a top sheet of hydrophobic material.

The Tunc patent discloses a fabric structure for use in sanitary napkins or similar applications. The structure uses an absorbent core in between two outer layers.

The Johnson patent shows a perineal shield device which initially is flat, but may be folded to conform to a wearer's anatomy.

The Rollenhagen patent shows a lined panty which has a layer structure including a layer of stretch resistant plastic in between absorbent layers.

Although the above prior art patents have been generally useful for their intended purposes, they have been subject to one or more significant disadvantages.

Prior art male sanitary pads have been troublesome to store in that they are generally quite thick because they use overlapping layers. Additionally, such prior art designs have commonly required the making of a cylindrical tube of absorbent material. The manufacturing of a generally cylindrical absorbent tube has been thought necessary in order to properly surround the wearer's penis.

In addition to the generally bulky storage and relatively complex construction, prior art male sanitary pads have generally been relatively expensive to manufacture in view of the complexity of construction.

OBJECTS AND SUMMARY OF THE INVENTION

Accordingly, it is a primary object of the present invention to provide new and improved sanitary pads for men.

A further object of the present invention is to provide sanitary pads for men which are relatively simple and inexpensive in construction.

A further object of the present invention is to provide sanitary pads for men which are compact to allow them to be carried unobtrusively.

Yet another object of the present invention is to provide sanitary pads for men which will readily maintain their operative (accident-consealing) position.

The above and other objects of the present invention which will become apparent as the description proceeds are realized by a sanitary pad for men comprising: a layered body portion including a relatively thick layer of absorbent material disposed on a first face of the body portion and having an internal surface opposite to the first face, a fluid barrier layer and attached to the internal surface, and a relatively thin layer of absorbent material disposed on a second face of the body portion opposite the first face and attached to the fluid barrier layer; and first adhesive means mounted to the body portion; and wherein the body portion is completely bounded by a plurality of edges, the body portion ending at the plurality of edges, and wherein the sanitary pad is adapted for disposal in: I. a storage mode with the body portion non-overlapping, flat in a plane, and the plurality of edges all in the plane; and II. an enveloping mode with the body portion folded to be non-planar and at least partially envelop a wearer's penis and the adhesive means is operable to maintain the body portion in proper position. In the enveloping mode, the body portion is folded to include an inner arm adapted for disposal between the wearer's penis and skin and an outer arm adapted for disposal between the wearer's penis and his cloths. In the enveloping mode, at least the outer arm is curved longitudinally around the wearer's penis. In the enveloping mode, the inner and outer arms are separated by a first fold line substantially perpendicular to the lengthwise direction of the wearer's penis. In the enveloping mode, the first adhesive means is mounted to the outer arm and operable to adhere the sanitary pad to the clothes of the wearer. Alternately, the first adhesive means is operable to maintain the body portion in a proper shape.

In the storage mode, the body portion includes a relatively wide portion and a relatively narrow portion; and, in the enveloping mode, the narrow portion is folded to form a narrow semi-cylindrical portion constituting one of the inner and outer arms, and the wide portion is folded to form a wide semi-cylindrical portion constituting the other of the inner and outer arms and disposed at least partially around the narrow semi-cylindrical portion. The first adhesive means may constitute fabric loop and hook fasteners operable to hold the wide semi-cylindrical portion around the narrow semi-cylindrical portion.

Alternately, in the storage mode, the body portion includes first and second parallel long edges, a first short edge perpendicular to the first and second long edges, and a second short edge; and, in the enveloping mode, the first short edges is folded towards the second short edge and at least part of the first long edge is cylindrically curved towards the second long edge. In the enveloping mode, each of the first and second long edges forms a U-shape.

The thick and thin absorbent layers are both made of paper and the fluid barrier is plastic.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 1 shows a plane view of a first embodiment of the present invention.

FIG. 2 shows a cross-sectional view taken along lines 2—2 of FIG. 1.

FIG. 3 shows a perspective view of the first embodiment of the present invention being placed in an enveloping mode.

FIG. 4 shows a plane view of a second embodiment of the present invention in a storage mode.

FIG. 5 shows a cross-section view taken along lines 5—5 of FIG. 4.

FIG. 6 shows the embodiment of FIG. 4 being folded.

FIG. 7 shows the embodiment of FIG. 4 in an enveloping mode.

FIG. 8 shows a cross-sectional view taken along lines 8—8 of FIG. 7.

DETAILED DESCRIPTION OF THE DRAWINGS

FIG. 1 shows a first embodiment of the present invention. The sanitary pad 10 shown in FIG. 1 comprises a body portion 12 including a wide portion 12W separated from a narrow portion 12N by a prefold line 14. The prefold line 14 may include perforations or indentations or be otherwise made to promote the folding of narrow portion 12N to wide portion 12W along the line 14.

The wide portion 12W is bounded by right and left side edges 16R and 16L, transverse edge 16T, and close (i.e., close to the prefold line 14) transverse right and left edges 16CR and 16CL. The narrow portion 12N is bounded by right and left edges 18R and 18L, transverse edge 18T, and the prefold line 14.

An adhesive strip 22 (phantom line in FIG. 1) is disposed on the surface 20U (opposite surface 20N of FIG. 1) defined by the edges 16T, 16R, 16L, 16CR, 16CL and prefold line 14. Additionally, right and left prefold lines 24R and 24L which are respectively parallel and colinear with 18R and 18L may be included on the wide portion 12W. The prefold lines 24R and 24L may include perforations, indentations, or other means to promote folding which are well known in the art.

Right and left tabs 26R and 26L are mounted to the surface 20U. As shown in phantom line, the right tab 26R extends over part of the surface 20U, whereas the left tab 26L is simply attached at the edge 16L. However, if desired, both of these tabs may be constructed identically. Alternately, the tab 26L may be constructed as shown, whereas the tab 26R may be wholly located over the surface 20U (i.e., it would not extend beyond edge 16R). For any of the constructions, the tab 26R is adapted to mate with and attach to the tab 26L. Preferably, the tabs are reuseable adhesive means as, for example, fabric loop and hook fasteners as commonly sold under the trademark "Velcro".

In the position of FIG. 1, the sanitary pad 10 is disposed in a storage mode with the body portion 12 non-overlapping, flat in a plane (parallel to the plane of the view of FIG. 1), and the edges 16T, 16R, 16L, 16CR, 16CL, 18R, 18L and 18T all in the plane. The mode makes it suitable for carrying in one's pocket. As shown, the body portion 12 is completely bounded by these edges and ends at these edges. The preferred lengths of the edges are 16T:4", 16R and 16L:-3½", 16CR and 16CL:-2", and 18T:1".

Turning now to FIG. 2, the layered construction of the body portion 12 of the present invention will be discussed in detail. It should initially be noted that the body portion 12 will preferably have the same structure throughout both its wide portion 12W and its narrow portion 12N. Adjacent an inner surface 20N is a relatively thick high absorbency layer 28. The layer 28 is bounded by an internal surface 28N which is opposite to the face inner surface 20N. The layer 28 could have uniform thickness throughout or, alternately, could be slightly thicker adjacent the pre-fold line 14. A fluid barrier layer 30 is attached to the internal surface 28N. The remaining layer on the layered body portion is a relatively thin layer 32 of absorbent material. As shown, this thin absorbent material layer 32 is attached to the fluid barrier layer 30 and disposed on the outer face or surface 20U of the body portion 12. The layers 28, 30 and 32 may be attached together by contact cement at their edges. Alternately, they may be sewn together or attached in numerous other ways known in the art.

The absorbent layers 28 and 32 are preferably made of high wet strength paper material. Paper mat, absorbent paper tissue, or similar constructions may be used. If desired, the layers 28 and 32 may be constructed of paper constructed for use as high quality high absorbency paper toweling. If desired, cotton or other materials may be included or used for the absorbent layers 28 and 32.

The water barrier layer 30 comprises a plastic, such as polyethylene, membrane or film. Basically, this barrier layer 30 prevents moisture absorbed within the layer 28 from escaping into the layer 32.

Turning now to FIG. 3, the operation of the sanitary pad 10 will be explained. FIG. 3 shows a perspective view of the sanitary pad 10 as it is being placed in an enveloping mode. In the enveloping mode, the pad 10 is folded to form a generally cylindrical shape such that it may be used to envelope the penis of the wearer.

In order to place the sanitary pad 10 in the enveloping mode, the narrow portion 12N is folded towards the inside surface 20N of the wide portion 12W. The fold occurs along the perforations defining the fold line 14. Additionally, the edges 18L and 18R are brought together in a generally cylindrically curved fashion (as shown in FIG. 3), thereby forming a generally semi-cylindrical shape and having edge 18T forming a U-shape. The wing portions (right wing between fold line 24R and edge 16R, left wing between fold line 24L and edge 16L) are then folded towards each other to assume the position shown in FIG. 3. The edge 16T is now generally U-shaped and the wide portion 12W forms a wide generally semi-cylindrical portion.

From the position shown in FIG. 3, the wearer will place his penis in between the wide semi-cylindrical portion formed by portion 12W and the narrow semi-cylindrical portion formed by portion 12N. The pad 10 is oriented with edge 16T positioned at the junction of penis and scrotum. The penis is positioned in the cylinder created by folding 12N at line 14 so that edge 18T is approximately opposite edge 16T. Edge 16L is brought around so that edge 16R either lies close to or is overlapped by edge 16L by folding on lines 24L and 24R. By this maneuver the narrow semi-cylindrical portion 12N constitutes an outer arm (i.e., disposed between penis and clothes) enclosed by the wings of portion 12W. The wide semi-cylindrical portion 12W, part of which surrounds portion 12N, constitutes an inner arm in that another part of it is between the wearer's penis and his scrotum. The fabric loop/hook fasteners 26L and 26R hold the cylinder intact and constitute adhesive means to maintain the body portion 12 in proper position. The adhesive means constituted by fasteners 26L and 26R may be sufficient to maintain the body portion 12 in proper position simply by virtue of the fasteners 26R and 26L holding the wide portion 12W around the narrow portion 12N and, thus, enveloping the wearer's penis in between those two portions.

In addition to, or possibly alternately to, the adhesive means constituted by fasteners 26R and 26L, an adhesive layer 22 may be disposed on the surface 20U of the wide portion 12W. The adhesive layer 22 may include a release paper (not shown) overlying it. Upon removal of the release paper, the adhesive strip 22 may be used to hold the pad 10 to the underwear of the wearer. This would help maintain the body portion 12 in proper position by removably attaching it to the wearer's briefs, boxer shorts, or other underpants.

Turning now to FIGS. 4 and 5, an alternate embodiment of the present invention will be discussed. The alternate embodiment pad 110, includes many parts which are substantially similar to the embodiment of FIGS. 1-3. Accordingly, the pad 110 includes numerals in the 100 series with the same last two digits as the generally corresponding part of the first embodiment of the present invention.

FIG. 4 shows the alternate embodiment pad 110 in a storage mode with its body portion 112 non-overlapping, flat in a plane (parallel to the plane of view of FIG. 4), and a plurality of edges 116R, 116L, 116T, 118R, 118L and 118T all in that plane. (Right and left are with reference to the wearer which is why, for example, 116R is on the left side of FIG. 4.) Edges 116R, 116L, 118R, 118L and 118T are each preferably 3 inches. The edges completely bound the body portion 112 and the body portion 112 ends at these edges.

As shown in FIG. 4, the body portion 112 includes a fold line 114 (similar in function to the fold line 14 of FIG. 1) and outer and inner fold lines 150U and 150N respectively. Disposed between the outer fold line 150U and edge 116T is an outer arm portion 112U, whereas an inner arm portion 112N is disposed between the inner fold line 150N and the transverse edge 118T. The arms 112U and 112N are generally similar in function to the respective portions 12W and 12N in FIG. 1.

Turning now to FIG. 5, it will be readily appreciated that the layering structure of the pad 110 is identical to that of the pad 10 as shown in FIG. 2. A relatively thick highly absorbent layer 128 is disposed on an inner face 120N and has a fluid barrier layer 130 separating it from an outer relatively thin absorbent layer 132. The adhesive strip 122 is also shown in the cross-section view of FIG. 5 taken along lines 5—5 of FIG. 4. The pad 110 may be the same throughout or have an increased thickness of layer 128 adjacent the fold line 114.

As shown in FIG. 6, the pad 110 is being folded along its fold lines 114, 150N and 150U for disposal in its enveloping mode which is shown in FIG. 7.

Continuing to consider FIGS. 4-6, but also looking at the enveloping mode of FIG. 7 and FIG. 8, which is a cross-sectional view taken along lines 8—8 of FIG. 7, the enveloping mode of the alternate embodiment pad 110 will be explained. After the edge 116T is brought around adjacent the edge 118T by folding outer arm 112U relative to inner arm 112N at fold lines 114, 150N and 150U, the outer arm 112U may be folded into a U-shape in cross-section as shown in FIG. 7. In addition each surface forms a semi-cylinder as shown for outer portion 112U in FIG. 8. This is accomplished by bringing edges 116R and 116L and 118R and 118L closer in the fashion shown in FIG. 8.

In the enveloping mode of FIG. 7, the wearer's penis would be oriented with edge 118T at the junction of the penis and scrotum and edge 116T brought opposite edge 118T by completing the fold at 114. Specifically, the outer arm 112U would be disposed between the wearer's penis and his briefs, boxer shorts, or other underwear. The inner arm or semi-cylindrical portion 112N would be disposed between the wearer's penis and the skin of his scrotum, the penis being generally pointing down as is its orientation when wearing pad 10. Although the embodiment 110 of the present invention may optionally use fastening or adhesive means similar to 26R and 26L of pad 10, the pad 110 is generally designed for mild male problems. Accordingly, this design may simply rely upon the semi-cylindrical inner and outer arm portions 112U and 112N retaining their shape after folding. Further, the adhesive strip 122 may be used to maintain the stability of position of the pad 110 by attaching the pad 110 to the wearer's clothes. As shown, each of the long edges (116L and 118L together, 116R and 118R together) form a U-shape in FIG. 7.

Both of the pad designs 10 and 110, are preferably individually wrapped to facilitate carrying in pockets and to provide hygenic handling.

Although various specifics of the present invention have been described herein, it is to be understood that these are for illustrative purposes. Numerous modifications and adaptations will be readily apparent to those of ordinary skill in the art. Accordingly, the scope of the present invention should be determined by reference to the claims appended hereto.

What is claimed is:

1. A sanitary pad for men comprising: a layered body portion including a relatively thick layer of absorbent material disposed on a first face of said body portion and having an internal surface opposite to said first face, a fluid-barrier layer parallel and attached to said internal surface, and a relatively thin layer of absorbent material disposed on a second face of said body portion opposite said first face and attached to said fluid barrier layer, and first adhesive means mounted to said relatively thin layer of said body portion; and wherein said body portion is completely bounded by a plurality of edges, said body portion ending at said plurality of edges, and wherein said sanitary pad is adapted for disposal in:
   I. a storage mode with said body portion non-overlapping, flat in a plane, and said plurality of edges all in said plane; and
   II. an enveloping mode with said body portion folded to be non-planar and at least partially envelope a wearer's penis and said adhesive means operable to maintain said body portion in proper position and wherein, in said enveloping mode, said body portion is folded to include an inner arm adapted for disposal at least partially between the wearer's penis and skin and an outer arm adapted for disposal between the wearer's penis and his clothes, and each arm extends lengthwise along the wearer's penis, and wherein said first adhesive means is operable to adhere said sanitary pad to the clothes of the wearer.

2. The sanitary pad for men of claim 1 wherein, in said enveloping mode, at least said outer arm is curved longitudinally around the wearer's penis.

3. The sanitary pad for men of claim 2 wherein, in said enveloping mode, said inner and outer arms are separated by a first fold line substantially perpendicular to the lengthwise direction of the wearer's penis.

4. A sanitary pad for men comprising: a layered body portion including a relatively thick layer of absorbent material disposed on a first face of said body portion and having an internal surface opposite to said first face, a fluid-barrier layer parallel and attached to said internal surface, and a relatively thin layer of absorbent material disposed on a second face of said body portion opposite said first face and attached to said fluid barrier layer, and first adhesive means mounted to said body portion; and wherein said body portion is completely bounded by a plurality of edges, said body portion ending at said plurality of edges, and wherein said sanitary pad is adapted for disposal in:
I. a storage mode with said body portion non-overlapping, flat in a plane, and said plurality of edges all in said plane; and
II. an enveloping mode with said body portion folded to be non-planar and at least partially envelope a wearer's penis and said adhesive means operable to maintain said body portion in proper position, and wherein, in said enveloping mode, said body portion is folded to include an inner arm adapted for disposal at least partially between the wearer's penis and skin and an outer arm adapted for disposal between the wearer's penis and his clothes and each arm extending lengthwise along the wearer's penis and wherein, in said storage mode, said body portion includes a relatively wide portion and a relatively narrow portion, said relatively wide portion having right and left wings; and, in said enveloping mode, said narrow portion is folded to form a narrow generally semi-cylindrical portion constituting one of said inner and outer arms, and said wide portion is folded to form a wide generally semi-cylindrical portion constituting the other of said inner and outer arms and disposed at least partly around said narrow generally semi-cylindrical portion, and said wide portion is separated from said narrow portion by a fold disposed at an end of the pad nearest the tip of the wearer's penis.

5. The sanitary pad for men of claim 4 wherein, in said enveloping mode, said first adhesive means is operable to maintain said body portion in a proper shape.

6. The sanitary pad for men of claim 4 wherein said first adhesive means constitute fabric loop and hook fasteners operable to hold said wide generally semi-cylindrical portion around said narrow generally semi-cylindrical portion.

7. The sanitary pad for men of claim 1 wherein, in said storage mode, said body portion includes first and second parallel long edges, a first short edge perpendicular to said first and second long edges; and a second short edge and, in said enveloping mode, said first short edge is folded towards said second short edge and at least part of said first long edge is cylindrically curved towards said second long edge.

8. The sanitary pad for men of claim 7 wherein, in said enveloping mode, each of said first and second long edges forms a U-shape.

9. The sanitary pad for men of claim 1 wherein said thick absorbent material layer and said thin absorbent material layer are both made of paper, and said fluid-barrier layer is plastic.

10. The sanitary pad for men of claim 4 wherein, in said enveloping mode, said inner and outer arms are separated by a first fold line substantially perpendicular to the lengthwise direction of the wearer's penis.

11. The sanitary pad for men of claim 4 wherein said thick absorbent material layer and said thin absorbent material layer are both made of paper, and said fluid-barrier layer is plastic.

12. The sanitary pad for men of claim 1 wherein, in said enveloping mode, said inner arm and said outer arm each have an end and the end of said inner arm is freely movable relative to the end of said outer arm.

* * * * *